US012112407B2

(12) United States Patent
Shinoda et al.

(10) Patent No.: US 12,112,407 B2
(45) Date of Patent: Oct. 8, 2024

(54) IMAGE GENERATING APPARATUS, IMAGE GENERATING METHOD AND STORAGE MEDIUM

(71) Applicant: CANON MEDICAL SYSTEMS CORPORATION, Otawara (JP)

(72) Inventors: Kensuke Shinoda, Otawara (JP); Hideaki Kutsuna, Kawasaki (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 651 days.

(21) Appl. No.: 17/329,766

(22) Filed: May 25, 2021

(65) Prior Publication Data
US 2022/0005240 A1  Jan. 6, 2022

(30) Foreign Application Priority Data

Jul. 3, 2020  (JP) .................................. 2020-115873

(51) Int. Cl.
*G06T 11/00* (2006.01)
*A61B 5/00* (2006.01)
(Continued)

(52) U.S. Cl.
CPC ............ *G06T 11/006* (2013.01); *A61B 5/004* (2013.01); *A61B 5/055* (2013.01); *G06T 5/94* (2024.01);
(Continued)

(58) Field of Classification Search
CPC ..... G06T 5/008; G06T 7/0012; G06T 11/006; G06T 2207/30101; G06T 2207/10088;
(Continued)

(56) References Cited

U.S. PATENT DOCUMENTS 5,713,358 A * 2/1998 Mistretta ............ G01R 33/5635
324/309
2004/0008028 A1    1/2004 Horger et al.
(Continued)

FOREIGN PATENT DOCUMENTS

JP           10192252 A  *  7/1998
JP        2002-095640 A     4/2002
(Continued)

OTHER PUBLICATIONS

Japanese Office Action issued Nov. 14, 2023 in Japanese Patent Application No. 2020-115873, 4 pages.
(Continued)

*Primary Examiner* — Vu Le
*Assistant Examiner* — Tracy Mangialaschi
(74) *Attorney, Agent, or Firm* — Oblon, McClelland, Maier & Neustadt, L.L.P.

(57) ABSTRACT

An image generating apparatus according to an embodiment includes processing circuitry. The processing circuitry is configured to successively generate Magnetic Resonance (MR) images in a plurality of temporal phases by using a first reconstruction method. The processing circuitry is configured to determine a first temporal phase before MR images in all the temporal phases during a predetermined time period are generated. The processing circuitry is configured to generate an MR image in the first temporal phase determined by the determining unit, by using a second reconstruction method having a larger processing load than the first reconstruction method.

20 Claims, 3 Drawing Sheets

(51) Int. Cl.
 *A61B 5/055* (2006.01)
 *G06T 5/94* (2024.01)
 *G06T 7/00* (2017.01)

(52) U.S. Cl.
 CPC ........ *G06T 7/0012* (2013.01); *A61B 2576/02* (2013.01); *G06T 2207/10088* (2013.01); *G06T 2207/30101* (2013.01)

(58) Field of Classification Search
 CPC .. G06T 5/94; G01R 33/56325; G01R 33/561; G01R 33/5601; A61B 5/0037; A61B 5/055; A61B 5/004; A61B 2576/00; A61B 2576/02
 See application file for complete search history.

(56) References Cited

U.S. PATENT DOCUMENTS

| | | | |
|---|---|---|---|
| 2005/0177042 A1* | 8/2005 | Abe | G01R 33/563 600/431 |
| 2006/0183996 A1* | 8/2006 | Abe | G01R 33/5676 600/410 |
| 2010/0039110 A1 | 2/2010 | Takahashi et al. | |
| 2017/0219705 A1 | 8/2017 | Kobayashi et al. | |

FOREIGN PATENT DOCUMENTS

| | | |
|---|---|---|
| JP | 2004-041732 A | 2/2004 |
| JP | 2010-012294 A | 1/2010 |
| JP | 2010-104459 A | 5/2010 |
| JP | 2017-136353 A | 8/2017 |
| WO | WO 2004/080302 A1 | 9/2004 |
| WO | WO 2008/111416 A1 | 9/2008 |

OTHER PUBLICATIONS

Feng, L. et al. "Golden-angle radial sparse parallel MRI; Combination of compressed sensing, parallel imaging, and golden-angle radial sampling for fast and flexible dynamic volumetric MRI" Magnetic Resonance in Medicine 72, 2014, pp. 707-717.

"GRASP", The technology of Applying Compressed Sensing https://www.innervision.co.jp/sp/ad/suite/_siemens/technical_notes/180418 ; Jun. 22, 2020 (with English translation), 8 pages.

Japanese Office Action issued Mar. 12, 2024 in Japanese Patent Application No. 2020-115873, 4 pages.

* cited by examiner

ID generating apparatus, image generating method and storage medium

IMAGE GENERATING APPARATUS, IMAGE GENERATING METHOD AND STORAGE MEDIUM

CROSS-REFERENCE TO RELATED APPLICATIONS

This application is based upon and claims the benefit of priority from Japanese Patent Application No. 2020-115873, filed on Jul. 3, 2020; the entire contents of which are incorporated herein by reference.

FIELD

Embodiments described herein relate generally to an image generating apparatus, an image generating method and a storage medium.

BACKGROUND

Conventionally, as an example of imaging methods implemented by a Magnetic Resonance Imaging (MRI) apparatus to generate a Magnetic Resonance (MR) image with a short temporal resolution, known short temporal resolution imaging methods include a Golden-angle Radial Sparse Parallel (GRASP) method being an imaging method to which compression sensing is applied.

The short temporal resolution imaging methods such as the GRASP method above, however, have a problem where there is a long waiting period until an MR image in a specific temporal phase is obtained.

DETAILED DESCRIPTION

An image generating apparatus according to an embodiment includes a first generating unit, a determining unit, and a second generating unit. The first generating unit is configured to successively generate MR images in a plurality of temporal phases by using a first reconstruction method. The determining unit is configured to determine a first temporal phase before MR images in all the temporal phases during a predetermined time period are generated by the first generating unit. The second generating unit is configured to generate an MR image in the first temporal phase determined by the determining unit, by using a second reconstruction method having a larger processing load than the first reconstruction method.

Embodiments

Figure 1:
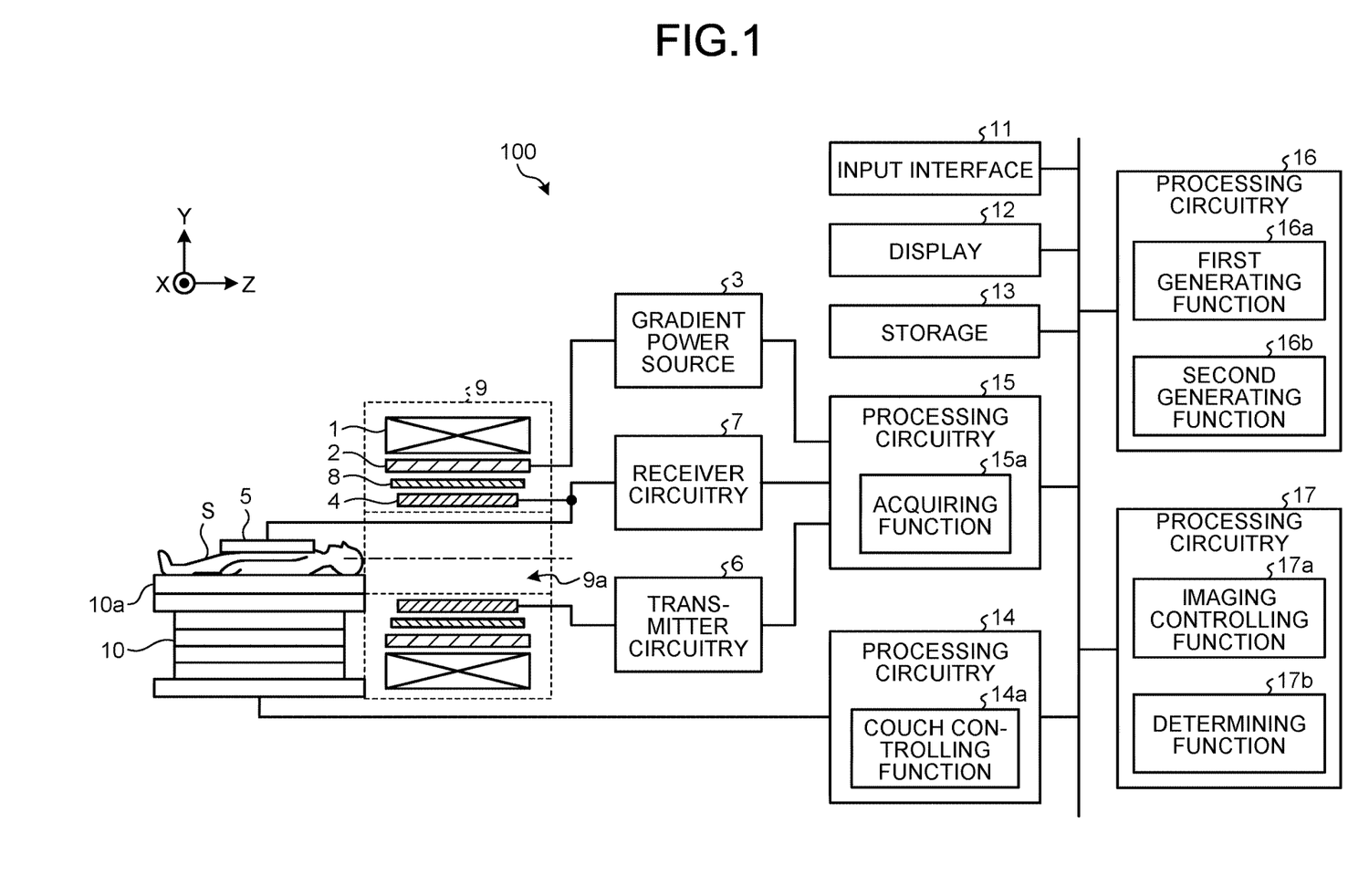
FIG. 1 is a diagram illustrating an exemplary configuration of an MRI apparatus according to an embodiment of the present disclosure.

FIG. 1 is a diagram illustrating an exemplary configuration of an MRI apparatus according to an embodiment of the present disclosure.

For example, as illustrated in FIG. 1, an MRI apparatus 100 includes a static magnetic field magnet 1, a gradient coil 2, a gradient power source 3, a whole body Radio Frequency (RF) coil 4, a local RF coil 5, transmitter circuitry 6, receiver circuitry 7, a Radio Frequency (RF) shield 8, a gantry 9, a couch 10, an input interface 11, a display 12, a storage 13, and pieces of processing circuitry 14 to 17.

The static magnetic field magnet 1 is configured to generate a static magnetic field in an imaging space in which an examined subject (hereinafter, "patient") S is placed. More specifically, the static magnetic field magnet 1 is formed to have a hollow and substantially circular cylindrical shape (which may have an oval cross-section orthogonal to the central axis thereof) and is configured to generate the static magnetic field in the imaging space formed on the inner circumferential side thereof. For example, the static magnetic field magnet 1 may be a superconductive magnet, a permanent magnet, or the like. In the present example, the superconductive magnet may be structured by using, for instance, a container filled with a cooling member such as liquid helium and a semiconductor coil immersed in the container.

The gradient coil 2 is arranged on the inside of the static magnetic field magnet 1 and is configured to generate gradient magnetic fields in the imaging space in which the patient S is placed. More specifically, the gradient coil 2 is formed to have a hollow and substantially circular cylindrical shape (which may have an oval cross-section orthogonal to the central axis thereof) and includes an X coil, a Y coil, and a Z coil respectively corresponding to an X-axis, a Y-axis, and a Z-axis that are orthogonal to one another. The X coil, the Y coil, and the Z coil are configured to generate, in the imaging space, the gradient magnetic fields that linearly change along the respective axial directions, on the basis of electric currents supplied thereto from the gradient power source 3. In this situation, the Z-axis is set along a magnetic flux in the static magnetic field generated by the static magnetic field magnet 1. Further, the X-axis is set along a horizontal direction orthogonal to the Z-axis. The Y-axis is set along a vertical direction orthogonal to the Z-axis. Accordingly, the X-axis, the Y-axis, and the Z-axis structure an apparatus coordinate system unique to the MRI apparatus 100.

By supplying the electric currents to the gradient coil 2, the gradient power source 3 is configured to cause the gradient magnetic fields to be generated within the imaging space. More specifically, by individually supplying the electric current to each of the X, Y, and Z coils in the gradient coil 2, the gradient power source 3 is configured to cause the gradient magnetic fields to be generated in the imaging space, so as to linearly change along a readout direction, a phase encode direction, and a slice direction, respectively, that are orthogonal to one another. In the following sections, the gradient magnetic field along the readout direction will be referred to as a readout gradient magnetic field. The gradient magnetic field along the phase encode direction will be referred to as a phase encode gradient magnetic field. The gradient magnetic field along the slice direction will be referred to as a slice gradient magnetic field.

In this situation, as each being superimposed on the static magnetic field generated by the static magnetic field magnet 1, the readout gradient magnetic field, the phase encode gradient magnetic field, and the slice gradient magnetic field append spatial position information to a magnetic resonance signal emitted from the patient S. More specifically, the readout gradient magnetic field appends position information along the readout direction to the magnetic resonance signal, by changing the frequency of the magnetic resonance signal in accordance with the position in the readout direction. Further, the phase encode gradient magnetic field appends position information along the phase encode direction to the magnetic resonance signal, by changing the phase of the magnetic resonance signal along the phase encode direction. In addition, the slice gradient magnetic field appends position information along the slice direction to the magnetic resonance signal. For example, the slice gradient magnetic field is used for determining the orientations, the thicknesses, and the quantity of slices when the imaged regions are two-dimensional slices and is used for changing the phase of the magnetic resonance signal in accordance with the position in the slice direction when the imaged region is three-dimensional volume. Accordingly, the axis along the readout direction, the axis along the phase encode direction, and the axis along the slice direction structure a logical coordinate system used for defining the slices or the volume subject to the imaging process.

The whole body RF coil 4 is arranged on the inner circumferential side of the gradient coil 2 and is configured to apply an RF magnetic field to the patient S placed in the imaging space and to receive the magnetic resonance signal emitted from the patient S due to influence of the RF magnetic field. More specifically, the whole body RF coil 4 is formed to have a hollow and substantially circular cylindrical shape (which may have an oval cross-section orthogonal to the central axis thereof) and is configured to apply the RF magnetic field to the patient S placed in the imaging space positioned on the inner circumferential side thereof, on the basis of an RF pulse signal supplied thereto from the transmitter circuitry 6. Further, the whole body RF coil 4 is configured to receive the magnetic resonance signal emitted from the patient S due to the influence of the RF magnetic field and to output the received magnetic resonance signal to the receiver circuitry 7.

The local RF coil 5 is configured to receive the magnetic resonance signal emitted from the patient S. More specifically, the local RF coil 5 is prepared for each site of the patient S and, when an imaging process is to be performed on the patient S, is arranged in the vicinity of the surface of the site to be imaged. Further, the local RF coil 5 is configured to receive the magnetic resonance signal emitted from the patient S due to the influence of the RF magnetic field applied by the whole body RF coil 4 and to output the received magnetic resonance signal to the receiver circuitry 7. In addition, the local RF coil 5 may further have the function of applying the RF magnetic field to the patient S. In that situation, the local RF coil 5 is connected to the transmitter circuitry 6 and is configured to apply the RF magnetic field to the patient S on the basis of the RF pulse signal supplied thereto from the transmitter circuitry 6. For example, the local RF coil 5 may be a surface coil or a phased array coil structured by combining together a plurality of surface coils as coil elements.

The transmitter circuitry 6 is configured to output the RF pulse signal corresponding to a Larmor frequency unique to targeted atomic nuclei placed in the static magnetic field, to the whole body RF coil 4. More specifically, the transmitter circuitry 6 includes a pulse generator, an RF generator, a modulator, and an amplifier. The pulse generator is configured to generate a waveform of the RF pulse signal. The RF generator is configured to generate an RF signal having a resonance frequency. The modulator is configured to generate the RF pulse signal by modulating the amplitude of the RF signal generated by the RF generator, with the waveform generated by the pulse generator. The amplifier is configured to amplify the RF pulse signal generated by the modulator and to output the amplified signal to the whole body RF coil 4.

The receiver circuitry 7 is configured to generate magnetic resonance data on the basis of the magnetic resonance signal output from either the whole body RF coil 4 or the local RF coil 5 and to output the generated magnetic resonance data to the processing circuitry 15. For example, the receiver circuitry 7 includes a selector, a pre-amplifier, a phase detector, and an analog/digital (A/D) converter. The selector is configured to selectively receive an input of the magnetic resonance signal output from either the whole body RF coil 4 or the local RF coil 5. The pre-amplifier is configured to amplify the magnetic resonance signal output from the selector. The phase detector is configured to detect the phase of the magnetic resonance signal output from the pre-amplifier. The A/D converter is configured to generate the magnetic resonance data by converting an analog signal output from the phase detector into a digital signal and to output the generated magnetic resonance data to the processing circuitry 15. In this situation, the processes described as being performed by the receiver circuitry 7 do not all necessarily have to be performed by the receiver circuitry 7. One or more of the processes (e.g., the process performed by the A/D converter) may be performed by either the whole body RF coil 4 or the local RF coil 5.

The RF shield 8 is arranged between the gradient coil 2 and the whole body RF coil 4 and is configured to shield the gradient coil 2 from the RF magnetic field generated by the whole body RF coil 4. More specifically, the RF shield 8 is formed to have a hollow and substantially circular cylindrical shape (which may have an oval cross-section orthogonal to the central axis thereof) and is arranged in the space on the inner circumferential side of the gradient coil 2 so as to cover the outer circumferential surface of the whole body RF coil 4.

The gantry 9 has a hollow bore 9a formed to have a substantially circular cylindrical shape (which may have an oval cross-section orthogonal to the central axis thereof) and houses therein the static magnetic field magnet 1, the gradient coil 2, the whole body RF coil 4, and the RF shield 8. More specifically, the gantry 9 houses these elements therein, while the whole body RF coil 4 is arranged on the outer circumferential side of the bore 9a; the RF shield 8 is arranged on the outer circumferential side of the whole body RF coil 4; the gradient coil 2 is arranged on the outer circumferential side of the RF shield 8; and the static magnetic field magnet 1 is arranged on the outer circumferential side of the gradient coil 2. In this situation, the space inside the bore 9a of the gantry 9 serves the imaging space in which the patient S is placed at the time of the imaging process.

The couch 10 includes a couchtop 10a on which the patient S is placed. When the imaging process is performed on the patient S, the couchtop 10a on which the patient S is placed is moved into the imaging space. For example, the couch 10 is installed so that the longitudinal direction of the couchtop 10a extends parallel to the central axis of the static magnetic field magnet 1.

In the present example, the MRI apparatus 100 has a so-called tunnel-like structure in which the static magnetic field magnet 1, the gradient coil 2, and the whole body RF coil 4 are each formed to have the substantially circular cylindrical shape; however, possible embodiments are not limited to this example. For instance, the MRI apparatus 100 may have a so-called open structure in which a pair of static magnetic field magnets, a pair of gradient coils, and a pair of RF coils are arranged so as to oppose each other, while the imaging space in which the patient S is placed is interposed therebetween. In the open structure, the space interposed between the pair of static magnetic field magnets, the pair of gradient coils, and the pair of RF coils corresponds to the bore in the tunnel-like structure.

The input interface 11 is configured to receive operations to input various types of instructions and various types of information from an operator. More specifically, the input interface 11 is connected to the processing circuitry 17 and is configured to convert the input operations received from the operator into electrical signals and to output the electrical signals to the processing circuitry 17. For example, the input interface 11 is realized by using a trackball, a switch button, a mouse, a keyboard, a touchpad on which an input operation can be performed by touching an operation surface thereof, a touch screen in which a display screen and a touchpad are integrally formed, a contactless input circuit using an optical sensor, an audio input circuit, and/or the like that are used for setting imaging conditions, a Region Of Interest (ROI), and the like. In the present disclosure, the input interface 11 does not necessarily have to include one or more physical operational component parts such as a mouse, a keyboard, and/or the like. Examples of the input interface 11 include, for instance, electrical signal processing circuitry configured to receive an electrical signal corresponding to an input operation from an external input device provided separately from the apparatus and to output the electrical signal to a control circuit.

The display 12 is configured to display various types of information. More specifically, the display 12 is connected to the processing circuitry 17 and is configured to convert data of various types of information sent thereto from the processing circuitry 17 into display-purpose electrical signals and to output the electrical signals. For example, the display 12 is realized by using a liquid crystal monitor, a Cathode Ray Tube (CRT) monitor, a touch panel, or the like. The display 12 is an example of a display unit.

The storage 13 is configured to store various types of data therein. More specifically, the storage 13 is connected to the processing circuitry 14 to 17 and is configured to store therein various types of data input and output by the processing circuitry 14 to 17. For example, the storage 13 is realized by using a semiconductor memory element such as a Random Access Memory (RAM) or a flash memory, or a hard disk, an optical disk, or the like.

The processing circuitry 14 includes a couch controlling function 14a. The couch controlling function 14a is configured to control operations of the couch 10 by outputting control-purpose electrical signals to the couch 10. For example, via the input interface 11, the couch controlling function 14a is configured to receive, from the operator, an instruction to move the couchtop 10a in a longitudinal direction, an up-and-down direction, or a left-and-right direction and to bring a moving mechanism of the couchtop 10a included in the couch 10 into operation, so as to move the couchtop 10a according to the received instruction.

The processing circuitry 15 includes an acquiring function 15a. The acquiring function 15a is configured to acquire k-space data by executing any of various types of pulse sequences. More specifically, the acquiring function 15a is configured to execute the various types of pulse sequences by driving the gradient power source 3, the transmitter circuitry 6, and the receiver circuitry 7 according to sequence execution data output from the processing circuitry 17. In this situation, the sequence execution data is data representing the pulse sequences and is information that defines: the timing with which the electric current is to be supplied by the gradient power source 3 to the gradient coil 2 and the intensity of the electric current to be supplied; the timing with which the radio frequency pulse signal is to be supplied by the transmitter circuitry 6 to the whole body RF coil 4 and the intensity of the radio frequency pulse to be supplied; the timing with which the magnetic resonance signal is sampled by the receiver circuitry 7; and the like. Further, the acquiring function 15a is configured to receive the magnetic resonance data output from the receiver circuitry 7 as a result of a pulse sequence being executed and to store the data into the storage 13. In this situation, the magnetic resonance data stored in the storage 13 is stored as k-space data corresponding to a two- or three-dimensional k-space, as a result of having appended thereto the position information along the directions of the readout direction, the phase encode direction, and the slice direction, by the readout gradient magnetic field, the phase encode gradient magnetic field, and the slice gradient magnetic field described above. The processing circuitry 16 includes a first generating function 16a and a second generating function 16b. The first generating function 16a and the second generating function 16b are configured to generate MR images from the k-space data acquired by the processing circuitry 15. More specifically, the first generating function 16a and the second generating function 16b are configured to generate two- or three-dimensional MR images by reading the k-space data acquired by the processing circuitry 15 from the storage 13 and performing a reconstruction process such as a Fourier transform on the read k-space data. After that, the first generating function 16a and the second generating function 16b are configured to store the generated MR images into the storage 13. The first generating function 16a and the second generating function 16b will be explained in detail later.

The processing circuitry 17 includes an imaging controlling function 17a and a determining function 17b. The imaging controlling function 17a is configured to control the entirety of the MRI apparatus 100 by controlling constituent elements of the MRI apparatus 100. More specifically, the imaging controlling function 17a is configured to cause the display 12 to display a Graphical User Interface (GUI) used for receiving operations to input various types of instructions and various types of information from the operator and to control the constituent elements of the MRI apparatus 100 in accordance with the input operations received via the input interface 11. For example, the imaging controlling function 17a is configured to cause the k-space data to be acquired, by generating the sequence execution data on the basis of the imaging conditions input by the operator and outputting the generated sequence execution data to the processing circuitry 15. Further, for example, by controlling the processing circuitry 16, the imaging controlling function 17a is configured to cause the MR images to be reconstructed on the basis of the k-space data acquired by the processing circuitry 15. Further, for example, in response to a request from the operator, the imaging controlling function 17a is configured to read any of the MR images stored in the storage 13 and to cause the display 12 to display the read MR images. The determining function 17b will be explained in detail later.

The exemplary configuration of the MRI apparatus 100 according to the present embodiment has thus been explained. The MRI apparatus 100 configured as described above has a function of implementing an imaging method by which a plurality of pieces of k-space data of which the signal intensities change in conjunction with temporal changes are acquired, so that MR images in arbitrary temporal phases and with arbitrary temporal resolution are generated from the plurality of pieces of k-space data.

For instance, examples of imaging processes that use the abovementioned imaging method include abdomen contrast-enhanced dynamic imaging. In the abdomen contrast-enhanced dynamic imaging, a contrast agent is administered for the patient, so as to acquire a plurality of pieces of k-space data of which the signal intensities change in conjunction with temporal changes due to the contrast agent. Further, from the acquired plurality of pieces of k-space data, for example, MR images in a number of main temporal phases are generated such as prior to the contrast enhancement, an arterial phase, a portal vein phase, a late phase, a hepatocellular phase, and the like. The temporal phases of the generated MR images are not limited to these temporal phases. The number of temporal phases in which the MR image are generated may also be arbitrary.

In this situation, the abdomen contrast-enhanced dynamic imaging does not allow re-take, because a contrast agent is used. Accordingly, it is important to generate the MR images with short temporal resolution in order to avoid missing the opportunity to capture temporal phases that are useful for a diagnosis process. For example, in the abdomen contrast-enhanced dynamic imaging, images in approximately 60 temporal phases can be acquired by starting the acquisition a little earlier than an inflow of the contrast agent, acquiring the data for approximately five minutes, and generating the MR images with temporal resolution of approximately five seconds. However, from a clinical viewpoint, MR images in the abovementioned main temporal phases are sufficient in almost all situations. In particular, short temporal resolution is required to capture the arterial phase.

Known examples of imaging methods for generating MR images with short temporal resolution as described above include short temporal resolution imaging methods such as the GRASP method to which compression sensing is applied.

The GRASP method is an imaging method using radial acquisitions and compression sensing. After pieces of k-space data are sequentially acquired in a time series, it is possible to generate MR images by retrospectively selecting data corresponding to an arbitrary number of spokes from arbitrary positions in the k-space. For example, it is possible to generate MR images with temporal resolution of 20 seconds by using data corresponding to approximately 140 spokes and also possible to generate MR images with temporal resolution of 1 to 2 seconds by using data corresponding to approximately 10 spokes.

However, the short temporal resolution imaging methods such as the GRASP method described above have a problem where there is a long waiting period until an MR image in a specific temporal phase is obtained.

For example, according to the GRASP method, the MR images are generated by implementing a reconstruction method using a total variation in the time direction. Accordingly, in order to select a specific temporal phase, it is necessary to wait until the MR images in all the temporal phases during a predetermined time period are generated. Further, it takes a long time to generate the images because the MR images are generated from undersampled data by performing iterative reconstruction. Furthermore, because the MR images in all the temporal phases during the predetermined time period need to be generated, the generated MR images are in a large volume. Accordingly, a storage with a large capacity is required to store the generated MR images.

In view of the circumstances described above, the MRI apparatus 100 according to the present embodiment is configured so that it is possible to obtain an MR image in a specific temporal phase with a short waiting period.

More specifically, the first generating function 16a of the processing circuitry 16 is configured to successively generate MR images in a plurality of temporal phases, by using a first reconstruction method. Further, the determining function 17b of the processing circuitry 17 is configured to determine a first temporal phase before MR images in all the temporal phases during a predetermined time period are generated by the first generating function 16a. Further, the second generating function 16b of the processing circuitry 16 is configured to generate an MR image in the first temporal phase determined by the determining function 17b, by using a second reconstruction method having a larger processing load than the first reconstruction method. In this situation, the first generating function 16a is an example of the first generating unit. The determining function 17b is an example of the determining unit. The second generating function 16b is an example of the second generating unit.

By using this configuration, it is possible to determine the specific temporal phase, without the need to wait until the MR images in all the temporal phases during the predetermined time period are generated. Consequently, according to the present embodiment, it is possible to obtain the MR image in the specific temporal phase with a short waiting period.

Next, a configuration of the MRI apparatus 100 according to the present embodiment will be explained in detail. In the following sections, an example of determining an arterial phase during the abdomen contrast-enhanced dynamic imaging will be explained. Hereinafter, the MR images generated by the first generating function 16a while using the first reconstruction method will be referred to as "simple reconstruction images", whereas the MR images generated by the second generating function 16b while using the second reconstruction method having a larger processing load than the first reconstruction method will be referred to as "diagnosis images".

The Acquiring Function:

To begin with, in the present embodiment, the acquiring function 15a is configured to acquire a plurality of pieces of k-space data of which the signal intensities change in conjunction with temporal changes.

More specifically, after a contrast agent is administered for the patient, the acquiring function 15a sequentially acquires the pieces of k-space data in a time series from the time period including at least an arterial phase and a late phase, by executing a pulse sequence set in advance for the abdomen contrast-enhanced dynamic imaging, on the liver serving as an imaged site.

For example, the acquiring function 15a acquires the pieces of k-space data that are successive in the time series, by implementing a data acquisition method such as a two- or three-dimensional radial acquisition, a two- or three-dimensional Cartesian acquisition, a spiral acquisition, or a stack-of-stars method.

The First Generating Function:

Further, in the present embodiment, by using the first reconstruction method, the first generating function 16a is configured to successively generate the simple reconstruction images in a plurality of temporal phases, from the plurality of pieces of k-space data which were acquired by the acquiring function 15a and of which the signal intensities change in conjunction with the temporal changes.

More specifically, the first generating function 16a successively generates the simple reconstruction images by using, as the first reconstruction method, a reconstruction method having a smaller processing load than the second reconstruction method (explained later) used by the second generating function 16b for generating the diagnosis images.

For example, the first generating function 16a successively generates the simple reconstruction images by using a method by which images are generated under simpler conditions than those used in the second reconstruction method. For example, the first generating function 16a successively generates the simple reconstruction images by using a Convolutional Neural Network (CNN), by selecting data corresponding to a certain number of spokes that makes it possible to distinguish an arterial phase from the k-space data acquired in a radial acquisition. Alternatively, the first generating function 16a may successively generate the simple reconstruction images by implementing parallel imaging, by selecting data corresponding to a certain number of readouts that makes it possible to distinguish an arterial phase from the k-space data acquired in an interleaved manner in a Cartesian acquisition. In yet another example, the first generating function 16a may successively generate images with a decreased number of matrices as the simple reconstruction images.

For example, when the k-space data has been acquired by implementing a three-dimensional data acquisition method, the first generating function 16a may generate, as the simple reconstruction images, multi-slice images including multiple slices that are successive in the thickness direction of the imaged region. In another example, when the k-space data has been acquired by implementing a two-dimensional data acquisition method, the first generating function 16a may generate, as the simple reconstruction images, a single-slice image.

The Determining Function:

Further, in the present embodiment, the determining function 17b is configured to determine the arterial phase before the first generating function 16a generates the simple reconstruction images in all the temporal phases during the predetermined time period. In this situation, the arterial phase is an example of the first temporal phase. The predetermined time period is a time period including at least an arterial phase and a late phase.

More specifically, the determining function 17b determines the arterial phase, on the basis of brightness changes corresponding to temporal phases in the simple reconstruction images successively generated by the first generating function 16a.

In this situation, as the brightness changes corresponding to the temporal phases in the simple reconstruction images, the determining function 17b uses brightness changes corresponding to temporal phases in the region of the aorta (hereinafter, "aorta region") included in the simple reconstruction images successively generated by the first generating function 16a.

More specifically, the determining function 17b detects the aorta region from the simple reconstruction images successively generated by the first generating function 16a and uses the brightness changes corresponding to the temporal phases in the detected aorta region, as the brightness changes corresponding to the temporal phases in the simple reconstruction images.

For example, at the point in time when the simple reconstruction image in the earliest temporal phase is reconstructed by the first generating function 16a, the determining function 17b causes the display 12 to display a temporal phase selection screen defined in advance.

Figure 2:
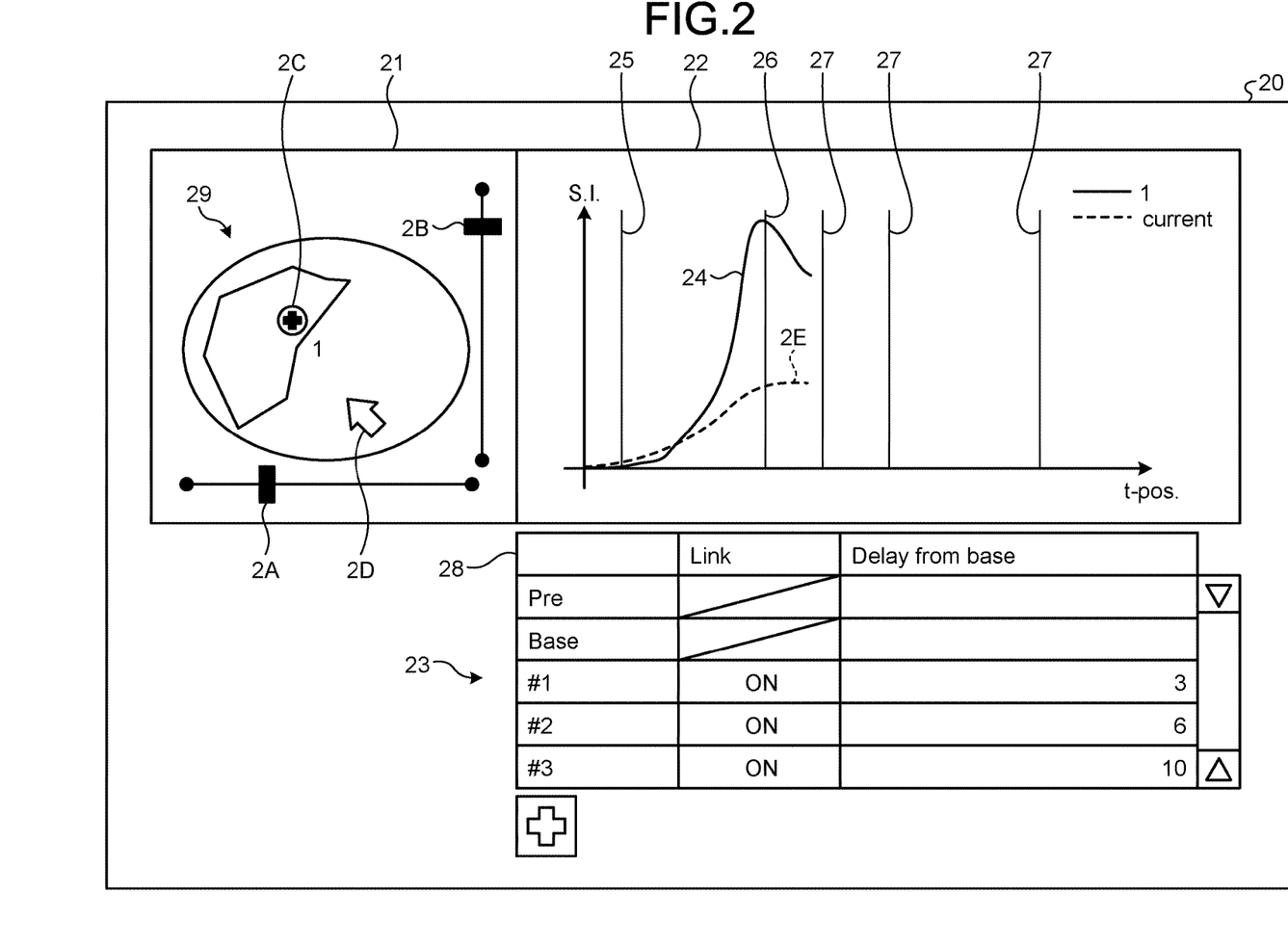
FIG. 2 is a drawing illustrating an example of a temporal phase selection screen 20 displayed by a determining function according to the present embodiment.

FIG. 2 is a drawing illustrating an example of a temporal phase selection screen 20 displayed by the determining function 17b according to the present embodiment.

For example, as illustrated in FIG. 2, the determining function 17b causes the display 12 to display the temporal phase selection screen 20 including a simple reconstruction image display region 21, a brightness change curve display region 22, and a temporal phase selection setting region 23.

Further, in the brightness change curve display region 22 on the temporal phase selection screen 20, the determining function 17b displays a curve 24 indicating the brightness changes corresponding to the temporal phases in the simple reconstruction images successively generated by the first generating function 16a (see the solid line "1" in FIG. 2). The curve indicating the brightness changes corresponding to the temporal phases will hereinafter be referred to as a "Time Intensity Curve (TIC)".

More specifically, the determining function 17b detects the aorta region from the simple reconstruction images successively generated by the first generating function 16a and further displays the TIC 24 in the detected aorta region, in the brightness change curve display region 22 on the temporal phase selection screen 20.

In this situation, for example, when the simple reconstruction images are multi-slice images, the determining function 17b selects a slice having the largest brightness values in the aorta region from among the plurality of slices and further displays the TIC 24 in the aorta region included in the selected slice.

Further, every time a simple reconstruction image is successively generated by the first generating function 16a, the determining function 17b successively updates the TIC 24 displayed in the brightness change curve display region 22 on the temporal phase selection screen 20. As a result, without the need to wait until the simple reconstruction images in all the temporal phases during the predetermined time period are generated, the TIC 24 displayed in the brightness change curve display region 22 on the temporal phase selection screen 20 is successively updated.

Further, in parallel to the TIC 24 being successively displayed on the temporal phase selection screen 20 as described above, the determining function 17b determines the arterial phase on the basis of the brightness changes corresponding to the temporal phases in the aorta region detected from the simple reconstruction images successively generated by the first generating function 16a.

For example, the determining function 17b determines a temporal phase in which the brightness change exhibits a peak, as the arterial phase. In another example, the determining function 17b may determine a temporal phase at the time when tens of seconds have elapsed since the brightness change started decreasing after reaching a peak, as the arterial phase. In yet another example, the determining function 17b may determine a temporal phase at the time when tens of seconds have elapsed since the brightness change started decreasing after reaching a peak, as the arterial phase. As a result, the arterial phase is automatically determined without the need to wait until the simple reconstruction images in all the temporal phases during the predetermined time period are generated.

Further, after determining the arterial phase, the determining function 17b determines another temporal phase different from the arterial phase on the basis of the determined arterial phase. In the following sections, an example will be explained in which, as the temporal phase different from the arterial phase, the determining function 17b determines the late phase, which is a temporal phase later than the arterial phase. In the present example, the late phase is an example of the second temporal phase.

More specifically, the determining function 17b determines the late phase before a simple reconstruction image in the late phase is generated by the first generating function 16a.

For example, the determining function 17b determines a temporal phase later than the determined arterial phase by a fixed delay time period set in advance, as the late phase. In this situation, the determining function 17b may determine a plurality of late phases on the basis of a plurality of delay time periods set in advance. As a result, when the arterial phase is determined, the late phase is determined without the need to wait until the one or more simple reconstruction images in the late phase are generated.

Further, when having determined the arterial phase and the late phase, the determining function 17b causes information indicating the determined arterial phase and late phase to be displayed on the temporal phase selection screen 20.

For example, as illustrated in FIG. 2, over the TIC 24 displayed in the brightness change curve display region 22 on the temporal phase selection screen 20, the determining function 17b displays a line 25 indicating the temporal position of a temporal phase prior to the contrast enhancement (hereinafter, "pre-contrast-enhancement phase"), as well as another line 26 indicating the temporal position of the arterial phase, and lines 27 indicating the temporal positions of the late phases.

Further, for example, in the temporal phase selection setting region 23 on the temporal phase selection screen 20, the determining function 17b displays a list 28 of the temporal phases displayed in the brightness change curve display region 22. For instance, in the example in FIG. 2, "Pre" denotes the pre-contrast-enhancement phase, whereas "Base" denotes the arterial phase. Further, "#1" denotes a late phase corresponding to a delay time period of "3" minutes; "#2" denotes a late phase corresponding to a delay time period of "6" minutes; and "#3" denotes a late phase corresponding to a delay time period of "10" minutes.

In this situation, the "ON" buttons displayed in the lines of "#1", "#2", and "#3" are buttons used for setting the delay time period ("Delay from base") for determining each of the late phases. For example, when the operator turns the button "ON", a prescribed delay time period set in each of the lines is used. When the operator turns the button "OFF", a delay time period entered by the operator is used.

Further, the button with the symbol "+" displayed underneath the list 28 of the temporal phases is a button for adding a late phase. Every time the button is pressed by the operator once, one late phase is added. In this situation, when a new late phase is added, a prescribed delay time period or a delay time period entered by the operator is set with the added late phase.

Furthermore, the determining function 17b causes a simple reconstruction image 29 in the arterial phase generated by the first generating function 16a to be displayed in the simple reconstruction image display region 21 on the temporal phase selection screen 20.

For example, every time a simple reconstruction image is successively generated by the first generating function 16a, the determining function 17b successively updates the simple reconstruction image 29 displayed in the simple reconstruction image display region 21 on the temporal phase selection screen 20. For example, the determining function 17b may successively update the simple reconstruction image 29 until the arterial phase is determined so as to stop updating the simple reconstruction image 29 at the point in time when the arterial phase is determined.

Further, for example, as illustrated in FIG. 2, in the simple reconstruction image display region 21, the determining function 17b displays a slider 2A used for forwarding temporal phases and further receives, from the operator, an operation to move the slider 2A. Further, in response to the received operation, the determining function 17b causes a simple reconstruction image in the corresponding temporal phase among the plurality of simple reconstruction images generated by the first generating function 16a to be displayed in the simple reconstruction image display region 21. As a result, the operator is able to reference a simple reconstruction image in any of the temporal phases, while changing from one temporal phase to another as appropriate.

Further, for example, as illustrated in FIG. 2, the determining function 17b displays, in the simple reconstruction image display region 21, a slider 2B used for forwarding the slices and further receives, from the operator, an operation to move the slider 2B. After that, in response to the received operation, the determining function 17b causes a corresponding slice among the plurality of slices included in the simple reconstruction images generated by the first generating function 16a to be displayed in the simple reconstruction image display region 21. As a result, when the simple reconstruction images are multi-slice images, the operator is able to reference any of the slices in different positions obtained in mutually the same temporal phases, while switching from one slice to another as appropriate.

Subsequently, via the input interface 11, the determining function 17b receives, from the operator, an indication as to whether or not the determined arterial phase and late phase are approved.

In this situation, when the arterial phase and the late phase are not approved by the operator, the determining function 17b changes the aorta region and the arterial phase according to an instruction from the operator.

More specifically, the determining function 17b receives, from the operator, an operation to designate a specific region in the simple reconstruction image 29 displayed in the simple reconstruction image display region 21 on the temporal phase selection screen 20 and further determines the region designated by the operation as the aorta region.

For example, the determining function 17b determines the aorta region, by receiving, from the operator, an operation to arrange an icon 2C indicating a Region Of Interest (ROI) over the simple reconstruction image 29, as the operation to designate the specific region.

Further, for example, as illustrated in FIG. 2, the determining function 17b further receives, from the operator, an operation to arrange a cursor 2D in an arbitrary position of the simple reconstruction image 29 displayed in the simple reconstruction image display region 21. After that, the determining function 17b further causes a TIC 2E corresponding to the position where the cursor 2D is arranged over the simple reconstruction image 29 to be displayed in the brightness change curve display region 22 on the temporal phase selection screen 20 (see the broken line indicated as "current" in FIG. 2). As a result, the operator is able to appropriately designate the aorta region, while referencing the TIC 2E in various positions within the simple reconstruction image 29, as appropriate.

After that, the determining function 17b updates the TIC 24 displayed in the brightness change curve display region 22 on the temporal phase selection screen 20, by generating a TIC of the post-change aorta region, on the basis of the simple reconstruction images generated by the first generating function 16a.

Further, the determining function 17b receives, from the operator, an operation to designate a specific temporal phase on the TIC 24 displayed in the brightness change curve display region 22 on the temporal phase selection screen 20 and further determines the temporal phase designated by the operation as an arterial phase.

For example, the determining function 17b may determines the arterial phase by receiving, from the operator, an operation to move the line 26 indicating the temporal position of the arterial phase displayed in the brightness change curve display region 22 on the temporal phase selection screen 20, as the operation to designate the specific temporal phase.

After that, on the basis of the post-change arterial phase, the determining function 17b determines, again, a temporal phase later than the arterial phase by the fixed delay time period set in advance, as the late phase. Alternatively, the determining function 17b may determine the late phase, for example, by receiving, from the operator, an operation to move the line 27 indicating the temporal position of the late phase displayed in the brightness change curve display region 22 on the temporal phase selection screen 20.

Further, the determining function 17b causes the simple reconstruction image 29 in the post-change arterial phase to be displayed in the simple reconstruction image display region 21 on the temporal phase selection screen 20.

After that, when the arterial phase and the late phase are approved by the operator, the second generating function 16b is instructed to generate a diagnosis image in the arterial phase and a diagnosis image in the late phase. The second generating function:

Further, in the present embodiment, according to an instruction from the determining function 17b, the second generating function 16b is configured to generate the diagnosis image in the arterial phase and the diagnosis image in the late phase determined by the determining function 17b, from the plurality of pieces of k-space data which were acquired by the acquiring function 15a and of which the signal intensities change in conjunction with the temporal changes, by using the second reconstruction method having a larger processing load than the first reconstruction method.

For example, as the second reconstruction method, the second generating function 16b generates the diagnosis image in each of the arterial and late phases, by using data corresponding to a larger number of spokes (in radial acquisitions) or a larger number of readouts (in Cartesian acquisitions) than in the first reconstruction method used by the first generating function 16a for generating the simple reconstruction images described above. For example, as the diagnosis images, the second generating function 16b may generate MR images in full size by using the data corresponding to all of the number of spokes or readouts acquired by the acquiring function 15a. In this situation, the value indicating the number of spokes or the number of readouts used for generating the diagnosis images is set in advance as one of the imaging conditions before the imaging process is started, for example. Alternatively, the second generating function 16b may generate the diagnosis images by complementing radio frequency components in the k-space with zeros.

Further, the second generating function 16b causes the display 12 to display the diagnosis images in the arterial phase and the diagnosis image in the late phase that were generated. As a result, only the diagnosis images in the temporal phases useful for the diagnosis process are displayed. It is therefore possible to reduce the load of image interpretation to be performed by the operator.

A Processing Procedure:

The processing functions of the pieces of processing circuitry 14 to 17 have thus been explained. For example, the pieces of processing circuitry are realized by one or more processors. In this situation, the processing functions of the pieces of processing circuitry are stored in the storage 13 in the form of computer-executable programs, for example. Further, the pieces of processing circuitry are configured to realize the processing functions corresponding to the programs, by reading and executing the programs from the storage 13. In other words, the pieces of processing circuitry that have read the programs have the functions illustrated within the pieces of processing circuitry in FIG. 1.

Figure 3:
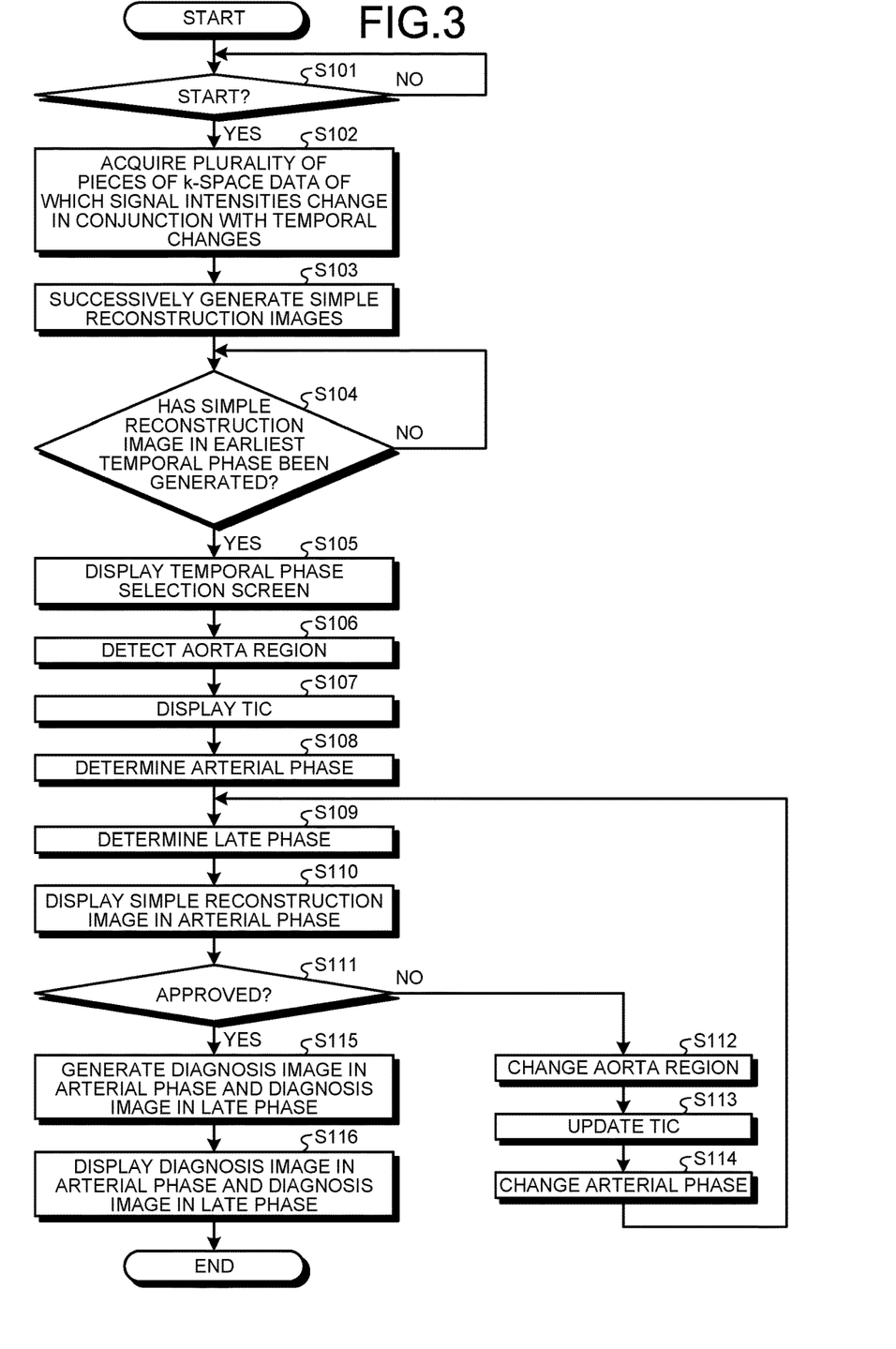
FIG. 3 is a flowchart illustrating a processing procedure of processes performed by processing functions included in processing circuitry of the MRI apparatus according to the present embodiment.

FIG. 3 is a flowchart illustrating a processing procedure of processes performed by the processing functions included in the processing circuitry of the MRI apparatus 100 according to the present embodiment.

For example, as illustrated in FIG. 3, in the present embodiment, upon receipt of an instruction to start the abdomen contrast-enhanced dynamic imaging from the operator (step S101: Yes), the imaging controlling function 17a starts the processes described below.

At first, the acquiring function 15a acquires a plurality of pieces of k-space data of which the signal intensities change in conjunction with temporal changes (step S102).

Further, by using the first reconstruction method, the first generating function 16a successively generates simple reconstruction images in a plurality of temporal phases, from the plurality of pieces of k-space data which were acquired by the acquiring function 15a and of which the signal intensities change in conjunction with the temporal changes (step S103).

Further, at the point in time when the simple reconstruction image in the earliest temporal phase is reconstructed by the first generating function 16a (step S104: Yes), the determining function 17b causes the display 12 to display the temporal phase selection screen defined in advance (step S105).

Further, the determining function 17b detects an aorta region from the simple reconstruction images successively generated by the first generating function 16a (step S106), so that the TIC 24 of the detected aorta region is displayed in the brightness change curve display region 22 on the temporal phase selection screen 20 (step S107).

After that, in parallel to the TIC 24 being successively displayed on the temporal phase selection screen 20, the determining function 17b determines the arterial phase, on the basis of the brightness changes corresponding to the temporal phases in the aorta region detected from the simple reconstruction images successively generated by the first generating function 16a (step S108).

Subsequently, on the basis of the determined arterial phase, the determining function 17b determines the late phase being a temporal phase later than the arterial phase (step S109).

Further, the determining function 17b causes the simple reconstruction image in the arterial phase generated by the first generating function 16a to be displayed in the simple reconstruction image display region 21 on the temporal phase selection screen 20 (step S110).

After that, the determining function 17b receives, from the operator, an indication as to whether or not the determined arterial phase and late phase are approved (step S111).

In this situation, when the arterial phase and the late phase are not approved by the operator (step S111: No), the determining function 17b changes the aorta region in accordance with an instruction from the operator (step S112).

After that, the determining function 17b updates the TIC 24 displayed in the brightness change curve display region 22 on the temporal phase selection screen 20, by generating a TIC of the post-change aorta region, on the basis of the simple reconstruction images generated by the first generating function 16a (step S113).

Further, in accordance with an instruction from the operator, the determining function 17b changes the arterial phase (step S114).

Subsequently, on the basis of the post-change arterial phase, the determining function 17b determines the late phase again (returns to step S109) and causes the simple reconstruction image in the post-change arterial phase to be displayed in the simple reconstruction image display region 21 on the temporal phase selection screen 20 (step S110).

After that, when the arterial phase and the late phase are approved by the operator (step S111: Yes), the second generating function 16b generates, by implementing the second reconstruction method having a larger processing load than the first reconstruction method, a diagnosis image in the arterial phase and a diagnosis image in the late phase determined by the determining function 17b, from the plurality of pieces of k-space data which were acquired by the acquiring function 15a and of which the signal intensities change in conjunction with the temporal changes (step S115).

Further, the second generating function 16b causes the display 12 to display the diagnosis image in the arterial phase and the diagnosis image in the late phase that were generated (step S116).

In this situation, the process at step S101 above is realized, for example, as a result of the processing circuitry 17 reading and executing a predetermined program corresponding to the imaging controlling function 17a from the storage 13. The process at step S102 is realized, for example, as a result of the processing circuitry 15 reading and executing a predetermined program corresponding to the acquiring function 15a from the storage 13. The process at step S103 is realized, for example, as a result of the processing circuitry 16 reading and executing a predetermined program corresponding to the first generating function 16a from the storage 13. The processes at steps S104 through S114 are realized, for example, as a result of the processing circuitry 17 reading and executing a predetermined program corresponding to the determining function 17b from the storage 13. The processes at steps S115 and S116 are realized, for example, as a result of the processing circuitry 16 reading and executing a predetermined program corresponding to the second generating function 16b from the storage 13.

Although the example was explained above in which the pieces of processing circuitry are each realized with a single processor, possible embodiments are not limited to this example. It is also acceptable to structure each of the pieces of processing circuitry by combining together a plurality of independent processors, so that each of the processing functions is realized as a result of the processors executing the programs. Further, the processing functions of the pieces of processing circuitry may be realized as being distributed among or integrated together in one or more pieces of processing circuitry, as appropriate. Further, although the example was explained with reference to FIG. 1 in which the single storage (the storage 13) stores therein the programs corresponding to the processing functions, it is also acceptable to provide a plurality of storages in a distributed manner, so that the processing circuitry reads a corresponding program from each of the individual storages.

As explained above, according to the present embodiment, the first generating function 16a is configured to successively generate the simple reconstruction images in the plurality of temporal phases by using the first reconstruction method. Further, the determining function 17b is configured to determine the arterial phase before the simple reconstruction images in all the temporal phases during the predetermined time period are generated by the first generating function 16a. Further, by using the second reconstruction method having a larger processing load than the first reconstruction method, the second generating function 16b generates the diagnosis image in the arterial phase determined by the determining function 17b.

With this configuration, in the abdomen contrast-enhanced dynamic imaging, it is possible to determine the arterial phase without the need to wait until the simple reconstruction images in all the temporal phases during the predetermined time period are generated. Consequently, according to the present embodiment, it is possible to obtain the MR image in the arterial phase with a short waiting period, in the abdomen contrast-enhanced dynamic imaging. As a result, the operator is able to promptly perform image interpretation.

Further, according to the present embodiment, there is no need to generate the simple reconstruction images in all the temporal phases during the predetermined time period. It is therefore possible to reduce the capacity of the storage required for storing therein the generated simple reconstruction images, in comparison to the situation where the simple reconstruction images in all the temporal phases during the predetermined time period are generated.

Modification Examples of the Embodiments

It is also possible to carry out the present embodiment, by changing a part of the configurations described above as appropriate. Thus, in the following sections, a number of modification examples of the embodiment described above will be explained.

For example, in the embodiment above, the example was explained in which the determining function 17b uses the brightness changes corresponding to the temporal phases in the aorta region included in the simple reconstruction images, as the brightness changes corresponding to the temporal phases in the simple reconstruction images successively generated by the first generating function 16a; however possible embodiments are not limited to this example.

For instance, the determining function 17b may use brightness changes corresponding to the temporal phases in the entire images of the simple reconstruction images, as the brightness changes corresponding to the temporal phases in the simple reconstruction images. As a result, it is possible to determine the arterial phase and to display a TIC more quickly than in the situation where the aorta region is detected from the simple reconstruction images.

Further, in the above embodiment, the example was explained in which the determining function 17b is configured to automatically detect the aorta region from the simple reconstruction images successively generated by the first generating function 16a; however, possible embodiments are not limited to this example.

For instance, instead of automatically determining the aorta region, the determining function 17*b* may be configured, similarly to the process of changing the aorta region described above, to receive from the operator an operation to designate a specific region within the simple reconstruction image 29 displayed in the simple reconstruction image display region 21 on the temporal phase selection screen 20 so as to determine the region designated by the operation as an aorta region.

Further, in the embodiment above, the example was explained in which the determining function 17*b* is configured to automatically determine the arterial phase, on the basis of the brightness changes corresponding to the temporal phases in the simple reconstruction images successively generated by the first generating function 16*a*; however, possible embodiments are not limited to this example.

For instance, instead of automatically determining the arterial phase, the determining function 17*b* may be configured, similarly to the process of changing the arterial phase described above, to receive from the operator an operation to designate a specific temporal phase on the TIC 24 displayed in the brightness change curve display region 22 on the temporal phase selection screen 20, so as to determine the temporal phase designated by the operation as an arterial phase.

Further, in the embodiment above, the example was explained in which the determining function 17*b* is configured to determine the arterial phase on the basis of the brightness changes corresponding to the temporal phases in the simple reconstruction images successively generated by the first generating function 16*a* and to further determine the late phase on the basis of the determined arterial phase; however, possible embodiments are not limited to this example.

For instance, on the basis of brightness changes corresponding to the temporal phases in the simple reconstruction images, the determining function 17*b* may determine the pre-contrast-enhancement phase and further determine the temporal phase of the arterial phase, which is a temporal phase later than the pre-contrast-enhancement phase, on the basis of the determined pre-contrast-enhancement phase. In this situation, the pre-contrast-enhancement phase is another example of the first temporal phase, whereas the arterial phase is another example of the second temporal phase.

In this situation, for example, the determining function 17*b* may determines the temporal phase at a time when the change amount of brightness changes per unit time period exceeds a predetermined change amount, as the pre-contrast-enhancement phase. Further, for example, the determining function 17*b* may determine a temporal phase later than the determined pre-contrast-enhancement phase by a fixed delay time period set in advance, as the arterial phase.

Further, in the embodiment above, the example was explained in which the determining function 17*b* is configured to determine the late phase, which is a temporal phase later than the arterial phase, as a temporal phase different from the arterial phase; however, possible embodiments are not limited to this example.

For instance, after determining the arterial phase, the determining function 17*b* may determine, on the basis of the determined arterial phase, a pre-contrast-enhancement phase, which is a temporal phase earlier than the arterial phase. In this situation, the pre-contrast-enhancement phase is another example of the second temporal phase.

In this situation, for example, the determining function 17*b* may determine a temporal phase earlier than the determined arterial phase by a fixed time period set in advance, as the pre-contrast-enhancement phase. As a result, when the arterial phase is determined, the pre-contrast-enhancement phase is automatically determined.

Further, in the embodiment above, the example was explained in which the determining function 17*b* is configured to display the TIC 24 of the simple reconstruction images at the point in time when the simple reconstruction image in the earliest temporal phase is reconstructed by the first generating function 16*a* and is configured, after that, to successively update the TIC 24 every time a simple reconstruction image is successively generated; however, possible embodiments are not limited to this example.

For instance, at the point in time of determining the arterial phase, the determining function 17*b* may display the TIC 24 in the brightness change curve display region 22 on the temporal phase selection screen 20. In that situation, the determining function 17*b* may keep displaying the TIC 24 corresponding to the point in time when the arterial phase is determined or may successively update the TIC 24 every time a simple reconstruction image is successively generated.

Further, in the embodiment above, the example was explained in which, when the acquiring function 15*a* has acquired the k-space data by implementing a three-dimensional data acquisition method, the first generating function 16*a* is configured to generate the multi-slice images as the simple reconstruction images; however, possible embodiments are not limited to this example.

For instance, when the k-space data has been acquired by implementing a three-dimensional data acquisition method, the first generating function 16*a* may generate, as a simple reconstruction image, an image of a slice having the largest brightness values in the aorta region, among the multiple slices that are successive in the thickness direction of the imaged region. As a result, the time required by the generation of the simple reconstruction image is shorter than the situation where the multi-slice images are generated as the simple reconstruction images. It is therefore possible to determine the arterial phase and to display the simple reconstruction image more quickly.

In yet another example, when the k-space data has been acquired by implementing a three-dimensional data acquisition method, the first generating function 16*a* may generate, as a simple reconstruction image, a Maximum Intensity Projection (MIP) image obtained by performing an MIP process on the k-space data in the thickness direction of the imaged region. In that situation, for example, the first generating function 16*a* generates one MIP image by using k-space data corresponding to a partial range in terms of the thickness direction of the imaged region. Alternatively, the first generating function 16*a* may generate a plurality of MIP images by dividing the imaged region into a plurality of ranges in the thickness region and further generating an MIP image for each of the divided ranges. In yet another example, the first generating function 16*a* may generate a plurality of MIP images by setting, with the imaged region, a plurality of ranges each having a predetermined size while shifting the position little by little in the thickness direction and further generating an MIP image for each of the set ranges.

In the above embodiment, the example was explained in which the abdomen contrast-enhanced dynamic imaging is performed; however, possible embodiments are not limited to this example. For instance, it is possible to determine a temporal phase useful for a diagnosis process, by similarly applying the abovementioned method to situations where another site or another organ is imaged.

Further, in the above embodiments, the example was explained in which the first generating unit, the determining unit, and the second generating unit of the present disclosure are realized with the first generating function 16a of the processing circuitry 16, the determining function 17b of the processing circuitry 17, and the second generating function 16b of the processing circuitry 16, respectively; however, possible embodiments are not limited to this example. For instance, instead of using the first generating function 16a, the determining function 17b, and the second generating function 16b described in the embodiments, it is also acceptable to realize the functions of the first generating unit, the second generating unit, and the determining unit of the present disclosure by using hardware only, software only, or a combination of hardware and software.

In the above explanations, the example was explained in which the one or more processors read and execute the programs corresponding to the processing functions from the storage; however, possible embodiments are not limited to this example. The term "processor" denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the one or more processors are each a CPU, for example, the processors realizes the processing functions by reading and executing the programs saved in the storage. In contrast, when the one or more processors are each an ASIC, instead of the programs being saved in the storage, the processing functions are directly incorporated in the circuits of the processors each as a logic circuit. The processors of the present embodiment do not each necessarily have to be structured as a single circuit. It is also acceptable to structure one processor by combining together a plurality of independent circuits so as to realize the processing functions thereof. Further, it is also acceptable to integrate two or more of the constituent elements illustrated in FIG. 1 into a single processor, so as to realize the processing functions thereof.

The programs executed by the one or more processors are provided as being incorporated in advance in a Read-Only Memory (ROM), storage, or the like. The programs may be provided as being recorded on a non-transitory computer-readable storage medium such as a Compact Disk Read-Only Memory (CD-ROM), a Flexible Disk (FD), a Compact Disk Recordable (CD-R), or a Digital Versatile Disk (DVD), in a file that is in an installable or executable format for the devices. Further, the programs may be stored in a computer connected to a network such as the Internet so as to be provided or distributed as being downloaded via the network. For example, the programs are structured as modules including the functional units described above. In actual hardware, as a result of a CPU reading and executing the programs from a storage medium such as a ROM, the modules are loaded into a main storage device so as to be generated in the main storage device.

According to at least one aspect of the embodiments described above, it possible to obtain the MRI image in the specific temporal phase with a short waiting period.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image generating apparatus, comprising:
processing circuitry configured to
successively generate, during a time period in which acquiring of magnetic resonance data corresponding to magnetic resonance signals emitted from a subject is being performed, a plurality of Magnetic Resonance (MR) images corresponding to different temporal phases, by a first reconstruction method, using the magnetic resonance data acquired in the time period;
determine, during the time period, a temporal phase in the time period, based on the MR images generated by the first reconstruction method, the temporal phase corresponding to an MR image to be generated by a second reconstruction method having a larger processing load than the first reconstruction method; and
generate, during the time period, the MR image corresponding to the determined temporal phase, by the second reconstruction method.

2. The image generating apparatus according to claim 1, further comprising:
a display configured to display a screen to designate a specific temporal phase in the time period, the specific temporal phase corresponding to the MR image to be generated by the second reconstruction method, wherein
the processing circuitry is further configured to determine, during the time period, as the temporal phase, the designated specific temporal phase on the screen, based on the different MR images generated by the first reconstruction method.

3. The image generating apparatus according to claim 2, wherein the display is further configured to display a curve indicating changes of brightness corresponding to the different temporal phases in the MR images generated by the first reconstruction method.

4. The image generating apparatus according to claim 3, wherein the processing circuitry is further configured to receive, from an operator, an operation to designate the specific temporal phase on the curve.

5. The image generating apparatus according to claim 2, wherein the display is further configured to display at least one of the MR images generated by the first reconstruction method.

6. The image generating apparatus according to claim 5, wherein the display is further configured to display a switcher to switch the temporal phase of the MR image to be displayed.

7. The image generating apparatus according to claim 2, wherein the display is further configured to display the MR image generated by the second reconstruction method.

8. The image generating apparatus according to claim 1, wherein the processing circuitry is further configured to determine, during the time period, the temporal phase corresponding to the MR image to be generated by the second reconstruction method, based on changes of brightness corresponding to the different temporal phases in the MR images generated by the first reconstruction method.

9. The image generating apparatus according to claim 1, wherein the processing circuitry is further configured to determine, during the time period, the temporal phase corresponding to the MR image to be generated by the second reconstruction method, based on changes of brightness corresponding to temporal phases in an aorta region included in the MR images generated by the first reconstruction method.

10. The image generating apparatus according to claim 9, wherein the processing circuitry is further configured to detect the aorta region, based on the MR images generated by the first reconstruction method.

11. The image generating apparatus according to claim 1, wherein the processing circuitry is further configured to:
   determine a first temporal phase as the temporal phase corresponding to the MR image to be generated by the second reconstruction method, based on the MR images generated by the first reconstruction method;
   determine a second temporal phase as the temporal phase corresponding to the MR image to be generated by the second reconstruction method, based on the first temporal phase; and
   generate a first MR image corresponding to the first temporal phase and a second MR image corresponding to the second temporal phase, by the second reconstruction method.

12. The image generating apparatus according to claim 11, wherein the processing circuitry is further configured to determine, as the second temporal phase, a temporal phase when a time set by an operator has elapsed since the first temporal phase.

13. The image generating apparatus according to claim 11, wherein the processing circuitry is further configured to determine the second temporal phase before the second MR image corresponding to the second temporal phase is generated.

14. The image generating apparatus according to claim 1, wherein a number of magnetic resonance data used in the second reconstruction method is larger than a number of magnetic resonance data used in the first reconstruction method.

15. An image generating method, comprising:
   successively generating, by processing circuitry, during a time period in which acquiring of magnetic resonance data corresponding to magnetic resonance signals emitted from a subject is being performed, a plurality of Magnetic Resonance (MR) images corresponding to different temporal phases, by a first reconstruction method,
   using the magnetic resonance data acquired in the time period;
   determining, by the processing circuitry, during the time period, a temporal phase in the time period, based on the MR images generated by the first reconstruction method, the temporal phase corresponding to an MR image to be generated by a second reconstruction method having a larger processing load than the first reconstruction method; and
   generating, by the processing circuitry, during the time period, the MR image corresponding to the determined temporal phase, by the second reconstruction method.

16. The image generating method according to claim 15, further comprising:
   displaying, by a display, a screen to designate a specific temporal phase in the time period, the specific temporal phase corresponding to the MR image to be generated by the second reconstruction method, wherein
   the determining step comprises determining, by the processing circuitry, during the time period, as the temporal phase, the designated specific temporal phase on the screen, based on the different MR images generated by the first reconstruction method.

17. The image generating method according to claim 16, further comprising displaying, by a display, a curve indicating changes of brightness corresponding to the different temporal phases in the MR images generated by the first reconstruction method.

18. The image generating method according to claim 17, further comprising receiving, by the processing circuitry, from an operator, an operation to designate the specific temporal phase on the curve.

19. The image generating method according to claim 16, further comprising displaying, by the display, at least one of the MR images generated by the first reconstruction method.

20. A non-transitory computer-readable storage medium having plural computer-executable commands recorded therein, the commands causing a computer to execute:
   successively generating, during a time period in which acquiring of magnetic resonance data corresponding to magnetic resonance signals emitted from a subject is being performed, a plurality of Magnetic Resonance (MR) images corresponding to different temporal phases, by a first reconstruction method, using the magnetic resonance data acquired in the time period;
   determining, during the time period, a temporal phase in the time period, based on the MR images generated by the first reconstruction method, the temporal phase corresponding to an MR image to be generated by a second reconstruction method having a larger processing load than the first reconstruction method; and
   generating, during the time period, the MR image corresponding to the determined temporal phase, by the second reconstruction method.

* * * * *